United States Patent [19]

Hochuli

[11] Patent Number: 4,551,271
[45] Date of Patent: Nov. 5, 1985

[54] PURIFICATION OF INTERFERON BY METAL CHELATE CHROMATOGRAPHY

[75] Inventor: Erich Hochuli, Arisdorf, Switzerland

[73] Assignee: Hoffmann-La Roche Inc., Nutley, N.J.

[21] Appl. No.: 584,286

[22] Filed: Feb. 27, 1984

[30] Foreign Application Priority Data

Mar. 3, 1983 [CH] Switzerland .......................... 1151/83
Dec. 13, 1983 [CH] Switzerland .......................... 6642/83

[51] Int. Cl.$^4$ .......................... C07G 7/00; A61K 45/02
[52] U.S. Cl. .................................. 260/112 R; 424/85
[58] Field of Search ...................... 260/112 R; 424/85

[56] References Cited

U.S. PATENT DOCUMENTS 4,257,938  3/1981  Hosoi et al. ................. 260/112 R
4,278,661  7/1981  Knight, Jr. ........................... 424/85
4,359,389  11/1982  Heine ................................ 424/85 X
4,440,675  4/1984  Braude ........................... 260/112 R

OTHER PUBLICATIONS

Handbook and General Catalog of Pierce Chemicals, (1983).
J. Biol. Chem., 252 (1977), 5934–5935, Edy et al.
Nature, 258, (1975), 598–599, Porath et al.
T. J. Gen. Virol., 43 (1979), 701–706, Chadha et al.
J. Chromatograph, 198, (1980), 247–255, Hubert et al.

Primary Examiner—Howard E. Schain
Attorney, Agent, or Firm—Jon S. Saxe; George M. Gould; William H. Epstein

[57] ABSTRACT

The purification of solutions of recombinant interferons is achieved by chromatography on metal chelate resins of the formula

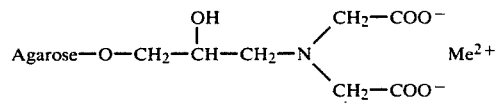

in which Me represents copper or nickel.

8 Claims, No Drawings

PURIFICATION OF INTERFERON BY METAL CHELATE CHROMATOGRAPHY

FIELD OF THE INVENTION

The present invention is concerned with a process for the purification of recombinant interferons by metal chelate chromatography and with the use of certain metal chelate resins for the purification of recombinant interferons.

BACKGROUND OF THE INVENTION

Under interferons there is to be understood a group of proteins which are specific to the body and which have antiviral and immunoregulatory activity. The antiviral effect is achieved not by a direct influence on the viruses themselves, but by an activity on their target cells in the sense of a protection against the virus infection. The interferons can exert objectifiable effects on cancer tumours, which make them suitable for use in cancer therapy, and they can influence the immune system of the body in that, for example, they activate macrophages and NK cells and intensify the expression of various immunologically significant constituents of the cell membrane.

Human interferons ($\alpha$, $\beta$ and $\gamma$) can today be prepared in a microbiological manner thanks to recombinant DNA technology in amounts which can not be made available by isolation from natural material (leucocytes, fibroblasts, lymphocytes) and purification in spite of the greatest efforts.

For the first time this new technology has opened a way for the intensive clinical testing and possible wide therapeutic use of interferons and an adequate supply of the active substances should appear feasible for persons seeking a treatment with the active substances.

Details of the cloning of interferon-cDNA and the direct expression thereof, especially in E. coli, have in the meanwhile been the subject of many publications. Thus, for example, the preparation of recombinant interferons is known, for example, from J. Interferon Res. 1 (1981), 381-390 (Wetzel et al.), Nature 284 (1980), 316-320 (Nagata et al,), Nucleic Acids Res. 8 (1980), 4057-4074 (Goeddel et al.), Nucleic Acids Res. 10 (1982), 2487-2501 (Devos et al.), Nature 295 (1982), 503-508 (Gray et al.), as well as from German Offenlegungsschriften Nos. 31 25 706, 31 38 096 and 31 44 469.

Since the recombinant interferons are of microbial origin (e.g. they are preferably derived from E. coli), after their isolation from the microorganism or from the culture medium they are initially still contaminated by a series of microbial impurities, the presence of which is prohibitive for a therapeutic use of the thus-produced interferons. The purification of the recombinant material therefore plays a particularly important role. A multitude of different methods, especially chromatography, have hitherto been used and combined with one another (see e.g. German Offenlegungsschrift No. 31 25 706) for the purification of recombinant interferons. Above all, chromatography on immunoadsorbents, namely on anti-interferon antibodies, has proved to be a valuable aid. Thus, the purification of recombinant human leucocyte interferon (HuIFN-$\alpha$) by means of monoclonal antibodies has been described, for example, by Staehelin et al. [J. Biol. Chem. 256 (1981), 9750-9754] and by Secher et al. [Nature 285 (1980), 446-450]. Having regard to the high specificity of these immunoadsorbents it must be assumed from this that the thus-purified material is practically free from contaminating substances and has a high degree of purity.

In the case of the purification of larger amounts of recombinant leucocyte interferon by means of monoclonal antibodies it has, however, been found that the purified material contains not only interferon fragments (interferon in which a part of the terminal amino acid sequence is missing), but also interferon oligomers, for example dimers. These undesirable byproducts have only a part of the biological activity of the pure interferon with comparable affinity to the antibodies.

A method for the purification of human fibroblast interferon (HuIFN-$\beta$) by means of a resin of the formula

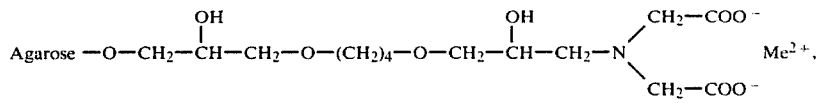

wherein Me signifies cobalt, nickel, zinc or copper, which is known from Nature 258 (1975), 598-599 (Porath et al.), has now been described in European Patent Apecification No. 11435. In addition, Edy et al. [J. Biol. Chem. 252 (1977), 5934-5935] have described the successful purification of HuIFN-$\beta$ on the zinc chelate resin described above. Chadha et al. [J. gen. Virol. 43 (1979), 701-706] subsequently showed that HuIFN-$\alpha$ can not be purified on the zinc copper chelate resins successfully employed in the case of HuIFN-$\beta$ and thus confirmed the observation previously made by Edy et al. (loc. cit.).

SUMMARY OF THE INVENTION

The present invention is a process for the purification of interferons, which process comprises bringing an interferon solution into contact with a metal chelate resin of the following structure

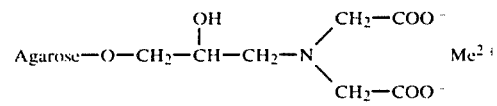

in which Me represents copper or nickel, and eluting the interferon in substantially pure form by treating the loaded resin with a washing liquid, and with the use of this metal chelate resin for the purification of interferons.

DETAILED DESCRIPTION OF THE INVENTION

In accordance with the invention it has now been found that the purification of recombinant interferons, irrespective of whether the interferon is IFN-$\alpha$, IFN-$\beta$ or IFN-$\gamma$, can be carried out by using in place of the metal chelate resin described by Porath et al. a resin of the formula

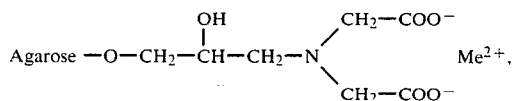

wherein Me signifies copper or nickel. This resin in principle has a similar structure to the Porath et al. resin, but is distinguished therefrom by a shorter distance between the agarose matrix and the iminodiacetic acid group. This resin and its preparation are already known, for example from J. Chromatography 198 (1980), 247–255 (Hubert and Porath). However, the authors describe its utility exclusively for the fractionation of oligonucleotides and polynucleotides, a class of compound which differs greatly from interferons so that it was in no manner obvious to the person skilled in the art to use it for the solution of the present problem of the purification of recombinant interferons, especially their separation from homologous sequence fragments and oligomers associated therewith.

The present invention is accordingly concerned with a process for the purification of recombinant interferons, which process comprises bringing an interferon solution, which preferably has already been partially purified, into contact with a metal chelate resin of the following structure

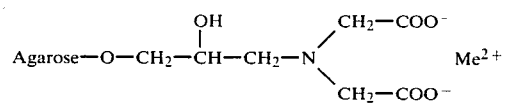

in which Me represents copper or nickel, and eluting the interferon in substantially pure form by treating the loaded resin with a washing liquid, and with the use of this metal chelate resin for the purification of recombinant interferons.

The metal chelate resin usable in accordance with the invention can be prepared in a known manner, as described, for example, by Hubert and Porath in J. Chromatog. 198 (1980), 247, by treating agarose with epichlorohydrin, reacting the resulting epoxide with iminodiacetic acid disodium salt and converting the product into the copper or zinc salt by washing with a copper (II) or zinc salt solution, for example with copper sulphate or zinc chloride. Epibromohydrin can be used in place of epichlorohydrin. As the agarose there is conveniently used a standardized product, preferably Sepharose ® from Pharmacia, Uppsala, Sweden. Sepharose ® 4B is especially preferred.

The preparation of a suitable copper chelate resin is illustrated in detail hereinafter:

One 1 of agarose gel (Sepharose ® 4B, Pharmacia) was washed on a glass frit twice with one 1 of water each time, transferred into a 4 1 reaction vessel and brought to a volume of 1000 ml with water. After adding 150 ml of 4N NaOH and 40 ml of epibromohydrin, the mixture was stirred at 30° C. for 5 hours. The activated resin was washed neutral on a glass frit with water, treated with 650 ml of aqueous 2N $Na_2CO_3$ solution and brought to a volume of 2000 ml with water. Then, 100 g of iminodiacetic acid disodium salt were added and the mixture was stirred at 65° C. for 20 hours. The resin was subsequently washed in a column in succession with in each case 200 ml of water, aqueous $CuSO_4.5H_2O$ (0.5 wt.%), water, 0.2M acetic acid (0.2M NaCl, 0.1 wt./vol.% Tween 20) and water. The copper ion concentration amounted to about 9 micromol/ml of resin.

Prior to the loading with interferon the metal chelate column is conveniently equilibrated with an aqueous buffer (pH about 5–8) which itself forms no chelate with copper or zinc, preferably a phosphate buffer pH 7. The equilibrating buffer (and also the elution buffer) can contain a stabilizer or emulsifier, for example of the polyoxyethylene-fatty alcohol ether type, the polyoxyethylenesorbitan-fatty acid ester type or Triton. The addition of such a stabilizer makes for a problem-free procedure even in the case of high interferon concentrations.

The nickel chelate resin can be prepared in an analogous manner using a nickel salt (e.g. $NiCl_2$).

The elution is carried out in a manner known per se with aqueous buffer solutions which do not chelate with copper or nickel, preferably with phosphate or acetate buffers, whereby the retention of the interferon fragments, the monomeric interferon and the oligomers is a function of the pH-value and of the ion strength. With falling pH-value and increasing ion strength there are firstly eluted the interferon fragments, then the monomeric interferon and finally, for example with dilute acetic acid, the oligomers. Within certain limits, which are familiar to the person skilled in the art, that the higher the ion strength of the elution buffer is chosen, then the higher can also be its pH-value. The ion strength of the buffer can be increased by adding neutral salts such as NaCl. By suitably adjusting the pH-value of the interferon solution containing the fragments and oligomers, for example to pH about 5, only the monomer and the oligomers are adsorbed, while the fragments flow through.

The elution can be carried out at a constant pH-value or with linear or discontinuously falling pH gradients. The optimum elution conditions depend on the amount and type of impurities present, the amount of material to be purified, the column dimensions etc and are conveniently determined on a case by case basis.

If the elution buffer contains stabilizers, then these can be removed by subjecting the eluate to chromatography on suitable carriers, for example on cellulose. Interferon purified in accordance with the invention can finally be crystallized from polyethylene glycol/water.

The purification of leucocyte interferon is preferably carried out on the copper chelate column and the purification of fibroblast interferon is preferably carried out on the nickel chelate column.

The following Examples illustrate the process in accordance with the invention.

The recombinant human leucocyte interferon A (rIFN-αA) used as the starting material was obtained by purification on monoclonal antibodies according to the method described by Staehelin et al. [J. Biol. Chem. 256 (1981), 9750–9754].

The human fibroblast interferon (rIFN-β), prepared according to the method of Goeddel et al. (Nucleic Acids Res. 8, 4057–4074 [1980]), used as the starting material was pre-purified by chromatography on immobilized triazine colouring substances (e.g. Blue-Sepharose CL-6B ® from Pharmacia or Blue Trisacryl M ® from LKB) according to the method of Friesen et al. (Arch. Biochem. Biophys. 206, 432–450 [1981]).

The determination of the protein content was carried out according to the method of Lowry et al. [J. Biol.

Chem. 193 (1951), 265–275] using serum albumin as the standard.

The quantitative derermination of the impurities (fragments and oligomers) was carried out by means of SDS-PAGE as described by Laemmli et al. [Nature 277 (1970), 680–685], with the modification that the electrophoresis was carried out under non-reducing conditions (i.e. without the addition of 2-mercaptoethanol to the sample).

EXAMPLE 1

A copper chelate column (169 ml, 5×8.5 cm) was equilibrated with 500 ml of phosphate buffer (0.05M, pH 7.0, 0.1 wt./vol.% Tween 20). The column was loaded at 4° C. with 1480 ml of an eluate from a monoclonal rIFN-αA-antibody column obtained according to Staehelin et al. (loc. cit.), which contained 0.28 mg/ml of protein (contaminated to 23.5 wt.% with a 15 kd interferon fragment) and which had been adjusted to pH 7 with 4N NaOH. The column was washed in succession with 300 ml of equilibrating buffer, 300 ml of equilibrating buffer additionally containing 0.2M NaCl, and with 300 ml of 0.05M acetate buffer pH 5.6 (containing 0.2M NaCl and 0.1% Tween 20). The interferon fragment was firstly eluted with a 0.05M acetate buffer (containing 0.2M NaCl and 0.1% Tween 20) at a pH gradient falling from 5.6 to 4.0. 256 mg of monomeric interferon (purity >95%) were then eluted with the same acetate buffer, pH 4.0.

The solution of the monomeric interferon containing 0.1 wt./vol.% Tween was chromatographed on a CM 52 cellulose column with a 0.1M ammonium acetate buffer (pH 5) in order to remove the stabilizer.

EXAMPLE 2

The same equilibrated copper chelate column as used in Example 1 was loaded at 4° C. with 2168 ml of an eluate from a monoclonal rIFN-αA-antibody column obtained in accordance with Staehelin et al. (loc. cit.), which contained 0.33 mg/ml of protein (contaminated to 27 wt.% with 15 kd interferon fragments) and which had been adjusted to pH 4.5 with 4N NaOH. The column was then washed with a 0.05M acetate buffer (pH 5.6; containing 0.2M NaCl and 0.1% Tween). Under these conditions only the entire 18.5 kd rIFN-αA, but not the 15 kd fragments, were adsorbed and subsequently eluted with a 0.05M acetate buffer (pH 4; 0.2M NaCl and 0.1% Tween 20). There were obtained 402 mg of interferon with a purity >95%.

EXAMPLE 3

The same equilibrated copper chelate column as used in Example 1 was loaded at 4° C. with 1260 ml of an eluate from a monoclonal rIFN-αA-antibody column obtained in accordance with Staehelin et al. (loc. cit.), which contained 0.5 mg/ml of protein (contaminated to 34 wt.% with interferon oligomers; a 37 kd dimer, a 55.5 kg trimer and a 74 kg tetramer) and which had been adjusted to pH 7 with 4N NaOH. The colum was firstly washed with 300 ml of a 0.05M phosphate buffer (pH 7; 0.1% Tween) and subsequently eluted with a 0.05M acetate buffer (pH 4.7; containing 0.2M NaCl and 0.1% Tween 20), there being obtained monomeric interferon with a purity of 95%. 150 mg of dimeric interferon were eluted with 0.05M acetate buffer of pH 4.0 (containing 0.2M NaCl and 0.1% Tween 20) and the higher oligomers were eluted with 0.2M acetate acid (containing 0.2M NaCl and 0.1% and 0.1% Tween 20).

EXAMPLE 4

A copper chelate column (295 ml, 5×15 cm) was equilibrated with 600 ml of phosphate buffer (0.05M, pH 7, 0.1% Tween 20). The column was loaded at 4° C. with 3200 ml of an eluate from a monoclonal rIFN-αA-antibody column obtained in accordance with Staehelin et al. (loc. cit.), which contained 0.33 mg/ml of protein (contaminated to 24 wt.% with a 15 kd interferon fragment and to 11 wt.% with interferon oligomers). The 15 kd fragment was removed by washing with a 0.005M acetate buffer (pH 4; 0.025M NaCl, 0.1% Tween 20). Monomeric interferon was eluted with 0.025M acetate buffer (pH 3.4; 0.025M NaCl, 0.1% Tween 20), there being obtained a total of 470 mg with a purity >95%. Finally, the oligomers were eluted with 0.2M acetic acid (0.2M NaCl, 0.1% Tween 20).

EXAMPLE 5

A copper chelate column (1000 ml, 10×13 cm) was equilibrated with 2500 ml of phosphate buffer (0.05M, pH 5, 0.2M NaCl, 0.1% Tween 20) and loaded at 4° C. with 10,000 ml of an eluate from a monoclonal rIFN-αA-antibody column obtained in accordance with Staehelin et al. (loc. cit.), which contained 0.21 mg/ml of protein (contaminated to 3 wt. % with a 15 kd interferon fragment and to 7 wt.% with interferon oligomers) and which had been adjusted to pH 7 with 6N NaOH. The fragment was removed by washing with the equilibrating buffer. 1700 mg of monomeric interferon (purity >95%) were eluted with 0.05M acetate buffer (pH 4.5, 0.2M NaCl, 0.1% Tween 20). The oligomers were obtained by elution with 0.2M acetic acid (0.2M NaCl, 0.1% Tween 20). For concentration and removal of the 0.1 wt./vol.% Tween 20, the solution of the monomeric interferon was chromatographed on a CM 52 cellulose column with 0.1M ammonium acetate buffer (pH 5).

48.7 ml of an aqueous solution of polyethylene glycol 4000 (0.3 g/ml) was added slowly at 4° C. with slight stirring to 195 ml of the eluate from the cellulose column, containing 4 mg/ml of protein. After about 5 hours, the first crystals formed and they were separated from the supernatant by centrifugation after 3 days in the cold, washed with cold aqueous polyethylene glycol 4000 (0.3 g/ml) and dried under reduced pressure. Yield: 520 mg. By means of gel electrophoresis and bioassay of a sample obtained by dissolving a few crystals in 0.1M ammonium acetate buffer (pH 5) it could be demonstrated that the crystals obtained were pure intact rIFN-αA.

EXAMPLE 6

The copper ions were washed out from a copper chelate column (12 ml, 1.6×6 cm) with 20 ml of a 0.1M aqueous solution of ethylenediaminetetraacetic acid disodium salt and then with 100 ml of water. The column was subsequently washed in succession with in each case 36 ml of 0.05M NiCl$_2$ in water, water, 0.05M acetic acid (containing 0.5M NaCl) and water.

The thus-obtained nickel chelate column was equilibrated with 36 ml of phosphate buffer (0.05M, pH 7.2, 10 wt./vol.% ethylene glycol, 0.2M NaCl). 38 ml of an eluate from a Blue-Sepharose ® column obtained in accordance with Goeddel et al./Friesen et al. (loc. cit.), which contained 0.12 mg/ml of protein, were diluted with 152 ml of phosphate buffer (0.05M, pH 7.2) and added at 4° C. to the nickel chelate column. The column was washed with 72 ml of acetate buffer (0.05M, pH 7, 10 wt./vol.% propylene glycol, 0.2M NaCl and then eluted with acetate buffer (0.05M, pH 3.5, 10 wt./vol.% propylene glycol, 0.3M NaCl). 3.75 g of pure (purity >95%) fibroblast interferon were obtained. The column was subsequently washed with 0.05M acetic acid (containing 0.5M NaCl) and was again ready for use.

I claim:

1. A process for the purification of interferons, which process comprises bringing an interferon solution into contact with a metal chelate resin of the following structure

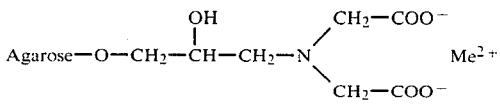

in which Me represents copper or nickel, and eluting the interferon in substantially pure form by treating the loaded resin with a washing liquid.

2. A process of claim 1, wherein the metal chelate resin is a copper chelate resin.

3. A process of claim 1, wherein the metal chelate resin is a nickel chelate resin.

4. The process of claim 2, wherein the inteferon is leucocyte interferon.

5. The process of claim 3, wherein the interferon is fibroblast interferon.

6. The process of claim 1, wherein the elution is a gradient elution.

7. The process of claim 6 wherein the pH of the washing liquid ranges from 5.6 to 4.0.

8. The process of claim 1, wherein the elution is carried out with an acetate buffer of pH 3.5.

* * * * *